United States Patent [19]

Kuether et al.

[11] 4,255,022

[45] Mar. 10, 1981

[54] METHOD OF AND APPARATUS FOR EXAMINATION OF VISUAL FIELDS

[75] Inventors: Christian L. Kuether, Houston; Robert E. Williams, Pearland; Thomas A. Decker; Charles Kurtzman, both of Houston, all of Tex.; Kenneth T. Richardson, Anchorage, Ak.; Richard A. Harrison, Houston, Tex.

[73] Assignee: Baylor College of Medicine, Houston, Tex.

[21] Appl. No.: 948,115

[22] Filed: Oct. 2, 1978

[51] Int. Cl.³ .............................................. A61B 3/06
[52] U.S. Cl. ........................................ 351/24; 351/36
[58] Field of Search .................. 351/23, 24, 36, 39

[56] References Cited

U.S. PATENT DOCUMENTS

| | | | |
|---|---|---|---|
| 2,441,031 | 5/1948 | Papritz | 351/24 |
| 2,564,794 | 8/1951 | Shekels | 351/23 X |
| 2,837,964 | 6/1958 | Gambs | 351/24 |
| 3,025,755 | 3/1962 | Koetting | 351/23 X |
| 3,288,546 | 11/1966 | Gans | 351/24 |
| 3,421,498 | 1/1969 | Gans | 351/24 X |
| 3,664,732 | 5/1972 | Lynn | 351/24 X |
| 3,883,234 | 5/1975 | Lynn et al. | 351/23 |
| 3,982,828 | 9/1976 | Woolf | 351/23 |
| 4,145,123 | 3/1979 | Krahn | 351/23 X |
| 4,146,311 | 3/1979 | Murr | 351/24 |

*Primary Examiner*—Paul A. Sacher
*Attorney, Agent, or Firm*—Fulbright & Jaworski

[57] ABSTRACT

A microprocessor based instrument designed to retrofit into existing perimeters utilizing the mechanics and stimulus control aspects of the existing perimeter. The device includes an array board positioned adjacent the perimeter mechanical arm and includes a multiplicity of visual indicators spatially arranged in a composite pattern of testing locations required for one or more ophthalmic testing procedures. A processor is connected to the array board for sequentially actuating the visual indicators in accordance with the testing procedure whereby the operator guides a cursor attached to the perimeter mechanical arm to align with the actuated indicators and control the location of the perimeter test stimulus. The processor includes means for sensing the position of the cursor, silently presenting a light flash to the patient, and a memory which records the patient's responses. When the program test sequence has been completed, the missed locations on the array board actuate allowing the examiner to manually record the data on a printed form. Switching means are provided whereby manual presentation of test stimuli may be provided, the patient's response overridden, and previous trials retested.

8 Claims, 18 Drawing Figures

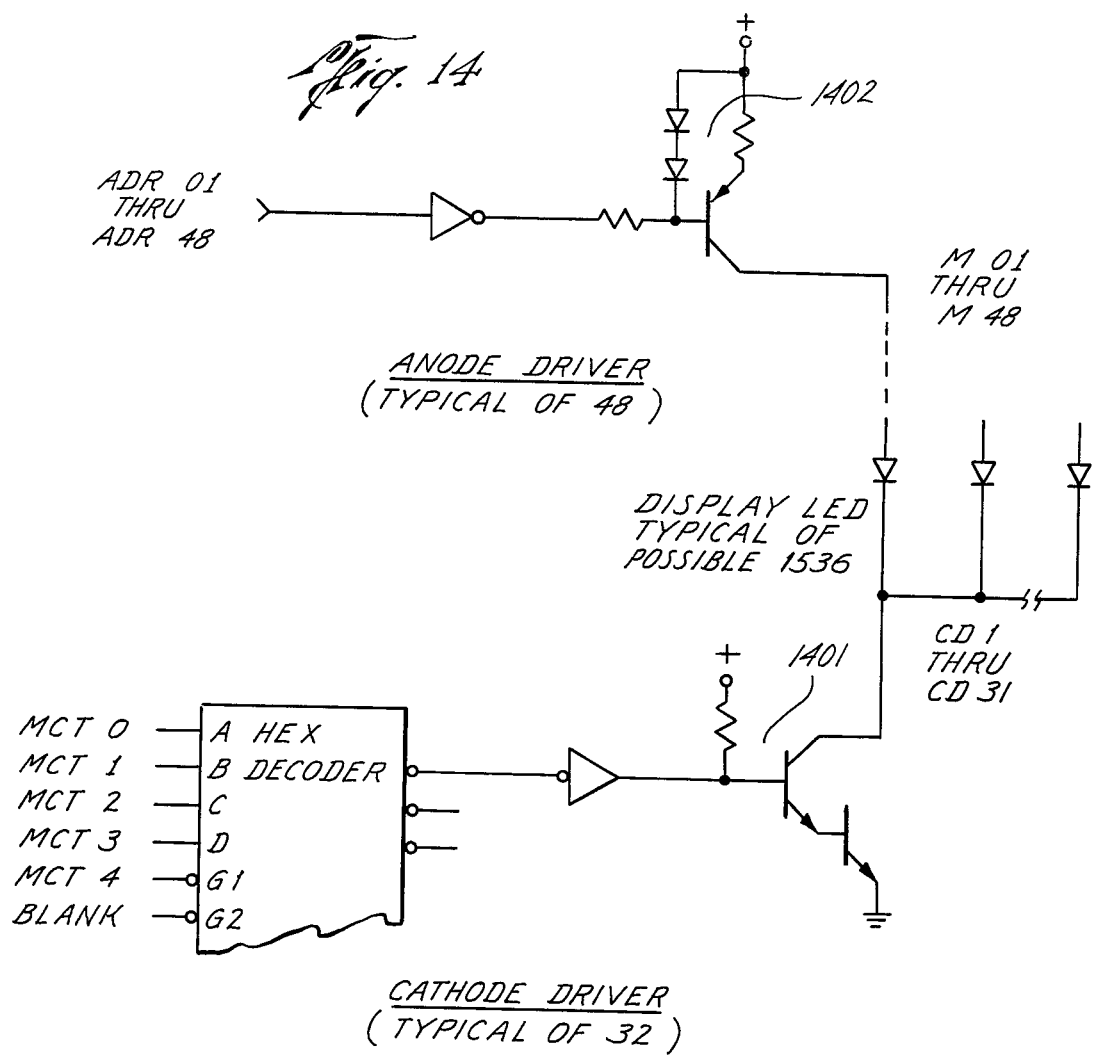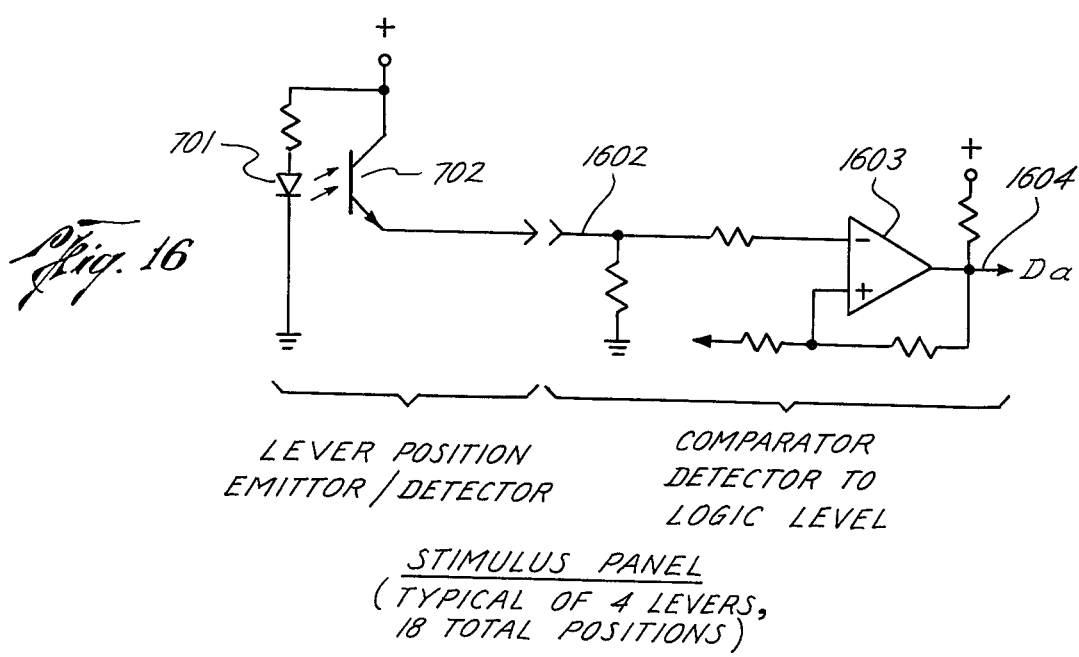

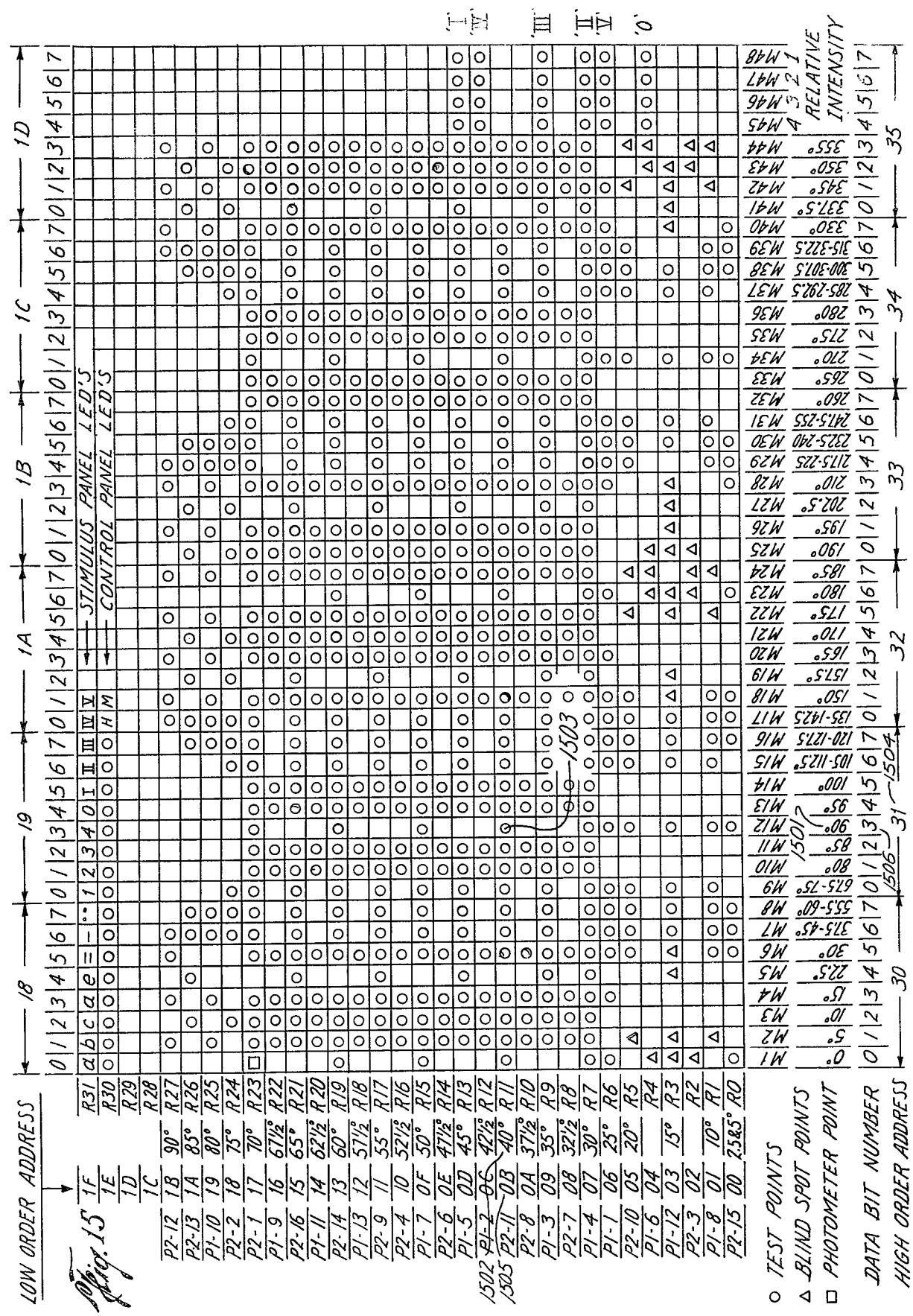

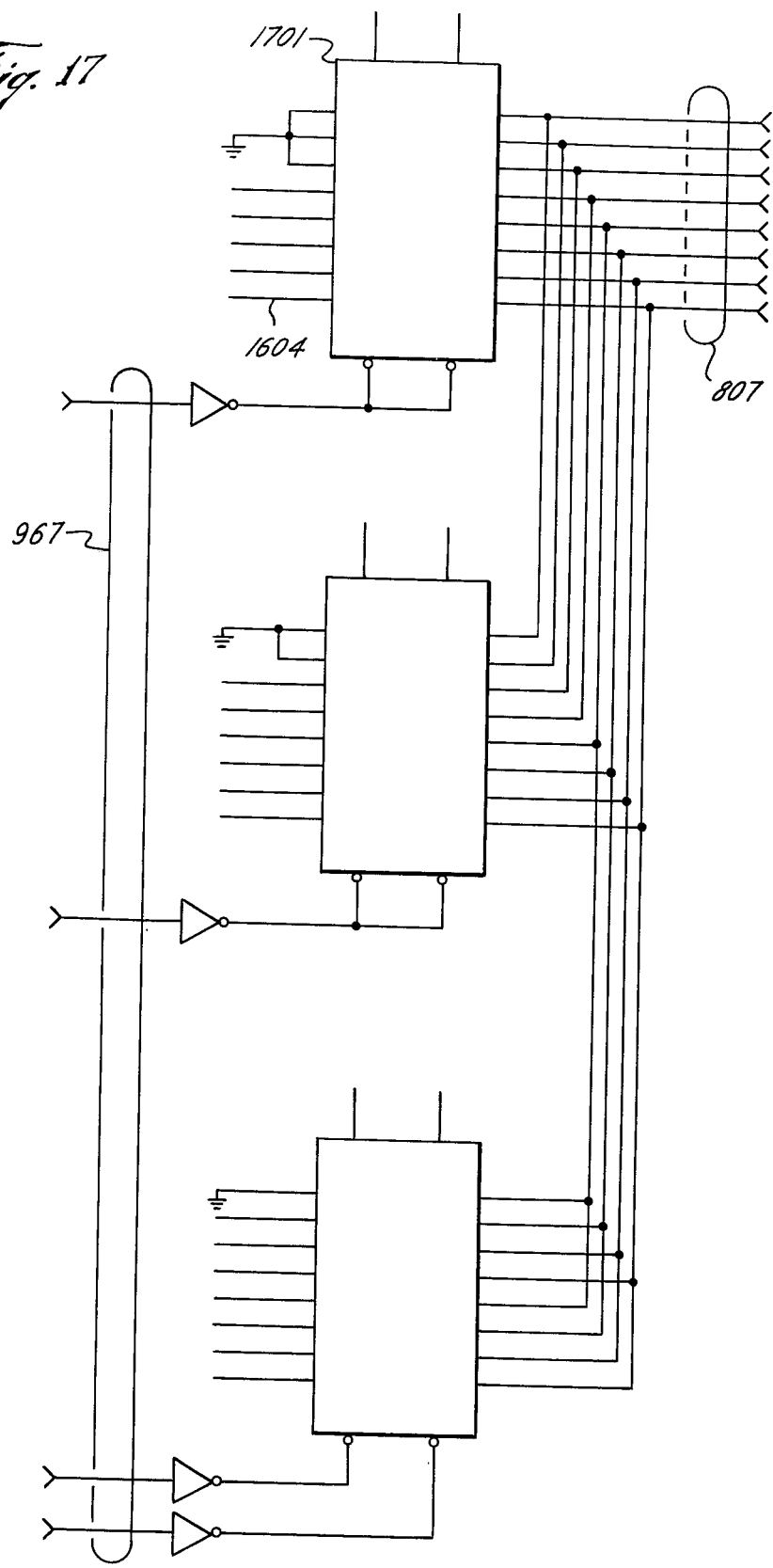

METHOD OF AND APPARATUS FOR EXAMINATION OF VISUAL FIELDS

BACKGROUND OF THE INVENTION

In the discipline of Ophthalmology one of the diagnostic tests used to test central and peripheral vision is commonly referred to as the "Visual Field Test." This test is performed utilizing a device popularly called a "perimeter." One of the perimeters in wide use and considered by many to be the clinical standard is the Goldmann-type dome perimeter.

Essentially the device consists of a hemisphere shaped dome into which the patient looks. A fixation light is provided to direct the patient's gaze toward the center of the dome while means are provided to locate the eye being tested near the center of curvature of the dome. In the test, stationary (static) or moving (kinetic) light stimuli are presented at various locations on the dome by means of an optical projection system. While gazing at the fixation light, the patient attempts to detect the presence of these stimuli, indicating that he has detected each stimulus by pressing a hand-held button.

In a typical examining procedure the examiner inserts a chart into a frame on the opposite side of the perimeter from the patient. The chart is printed with a pattern which represents the retinal areas of the patient's eye which may be stimulated by projecting the stimulus onto a corresponding location on the dome. The examiner directs the stimulus by means of the projection optics to the desired location on the dome by moving a pantograph arm attached to a pointer over the surface of the printed chart until the point is aligned with the retinal location selected for testing.

Prior to each stimulus or series of stimulus presentations, the operator looks into a telescope provided on the perimeter to make certain that the patient's eye is fixed on the fixation light. In static testing the examiner moves the pointer to the desired testing location, manually opens and closes a shutter delivering a light stimulus to the inside of the dome. Using the pointer as a guide, he then records on the chart paper whether the patient detected (eg. pressed his button) or did not detect the stimulus. A variation on this technique relates to kinetic testing in which the examiner positions the stimulus, holds the shutter open, and moves the stimulus inward (toward the patient's fixation) until a response occurs. The location of the pointer at the time of the patient's response is recorded manually on the chart paper as the patient's threshold point. The marked positions of all of the tested points on the chart define the field of vision of the eye tested for the size and luminance of the stimulus used. The size and luminance of the stimuli are adjustable by means of controls on the perimeter.

When carefully conducted the tests are accurate and definitive. Practically, however, a high degree of skill is required of the examiner and extensive training is necessary to insure sufficient test standardization to insure that the data obtained is valid and comparable to previously obtained data. Traditional visual fields testing devices leave a great degree of the responsibility for the conduct of the test in the hands of the technician. Moreover, omissions of stimulus positions, use of incorrect stimulus levels, varying duration of shutter operation, inappropriate rate of movement of the stimulus in kinetic testing and other procedural faults, whether occurring inadvertently or not, significantly reduce the clinical value of the test. Because the procedure is time consuming, tedious and boring, employee turnover in this area is often great, further compounding the problem of technician training. In some areas of the world the physician performs the visual fields testing himself, finding this the only way of insuring proper execution of the test.

SUMMARY

The present invention relates to a processor based electromechanical device designed to be attached to standard projection type visual field perimeters.

It is therefore one object of the invention to provide a device which may be attached to a perimeter to affect a means for standardizing visual fields testing procedures.

Another object of the invention is to provide a device which, when added to a visual fields instrument, does not interfere with the use of the perimeter for full fields testing in the traditional manner.

Another object is to provide a device which prompts the operator step by step through a predetermined sequence designed to assure that set-up procedures, threshold procedures and adjustments to stimulus levels have been carried out, and that all test locations have been tested, and all data have been recorded.

Yet another object of the invention is to provide a multiplicity of testing procedures from which the most appropriate can be selected for the needs of the individual patient.

Another object of the invention is to provide an array board of indicators individualy addressable by the system electronics and arranged spatially and located within the perimeter to correspond to testing locations on the patient's retina, said array board having the function of indicating to the operator where and when to test the patient.

A still further object of the invention is to provide array board controls to aid the operator in performing static testing (patient's threshold to brief, stationary test flash) and kinetic testing (patients' threshold to a light stimulus which moves from the periphery of his vision toward his fixation point).

A further object of the invention is to provide a means for preventing patient anticipation by presenting successive test locations on a spatially pseudo random basis.

An object of the invention is to provide a cursor to attach to the pantograph arm of the perimeter, said cursor containing means to sense alignment of the cursor over an illuminated indicator on the array board.

A further object of the invention is to provide a cursor with a switch which allows the operator to control certain aspects of the operation of the invention and an indicator to provide feedback to the operator as to the status of the system electronics.

Yet another object of the invention is to provide means to detect the setting of the levers which control the size and intensity of the stimulus and to provide indicators which signal the appropriate settings.

Another object of the invention is to use these stimulus lever indicators to show the operator which stimulus levels to use for differing parts of the patient's retina according to a preprogrammed threshold testing sequence or according to a stored standard stimulus paradigm.

Another object of the invention is to provide a silent shutter under control of the system electronics capable of delivering a precise, repeatable test flash of known duration, or a longer test exposure whose duration is controlled by the patient's response.

Yet another object of the invention is to allow the operator to determine whether test exposures to the patient will occur automatically after the cursor is aligned over the illuminated indicator on the array board or only after he has pushed the cursory pushbutton.

A further object of the invention is to provide automatic entry of patient data through a patient response pushbutton, and to classify the patient responses into "hits" (stimulus detected) and "misses" (stimulus not detected).

An object of the invention is to provide automatic storage of patient responses to each stimuli and to display the data stored to the operator when requested.

A further object is to provide means to repeat the just previous test and to change the classification of the patient's response.

Yet a further object of the invention is to allow the operator to recheck all missed points at the end of each segment of the testing procedure.

Another object of the invention is to display missed and threshold points at the end of the test for manual recording by the operator on special or standard recording charts.

A further object is to use a matrix of indicators on the array board to aid the operator to record and correlate the specific stimulus level used to obtain specific data points.

Another object of the invention is to provide independent use of the silent shutter for times stimulus exposures when the perimeter is being operated in a traditional manner and to allow independent use of the patient response pushbutton to signal a patient response under similar circumstances.

BRIEF DESCRIPTION OF THE DRAWINGS

FIG. 14 is a typical anode and cathode driver circuitry, FIG. 15 is a display table, FIG. 16 is a typical stimulus panel position detector circuits, FIG. 17 is a logic diagram of the stimulus panel interface.

DESCRIPTION OF THE EXEMPLARY EMBODIMENT

While the present invention is useful in various types of ophthalmic visual fields testing instrument, the present invention, for purposes of illustration only, will be described as attached to a Goldmann dome-type perimeter as more fully described in U.S. Pat. No. 2,441,031.

Figure 1:
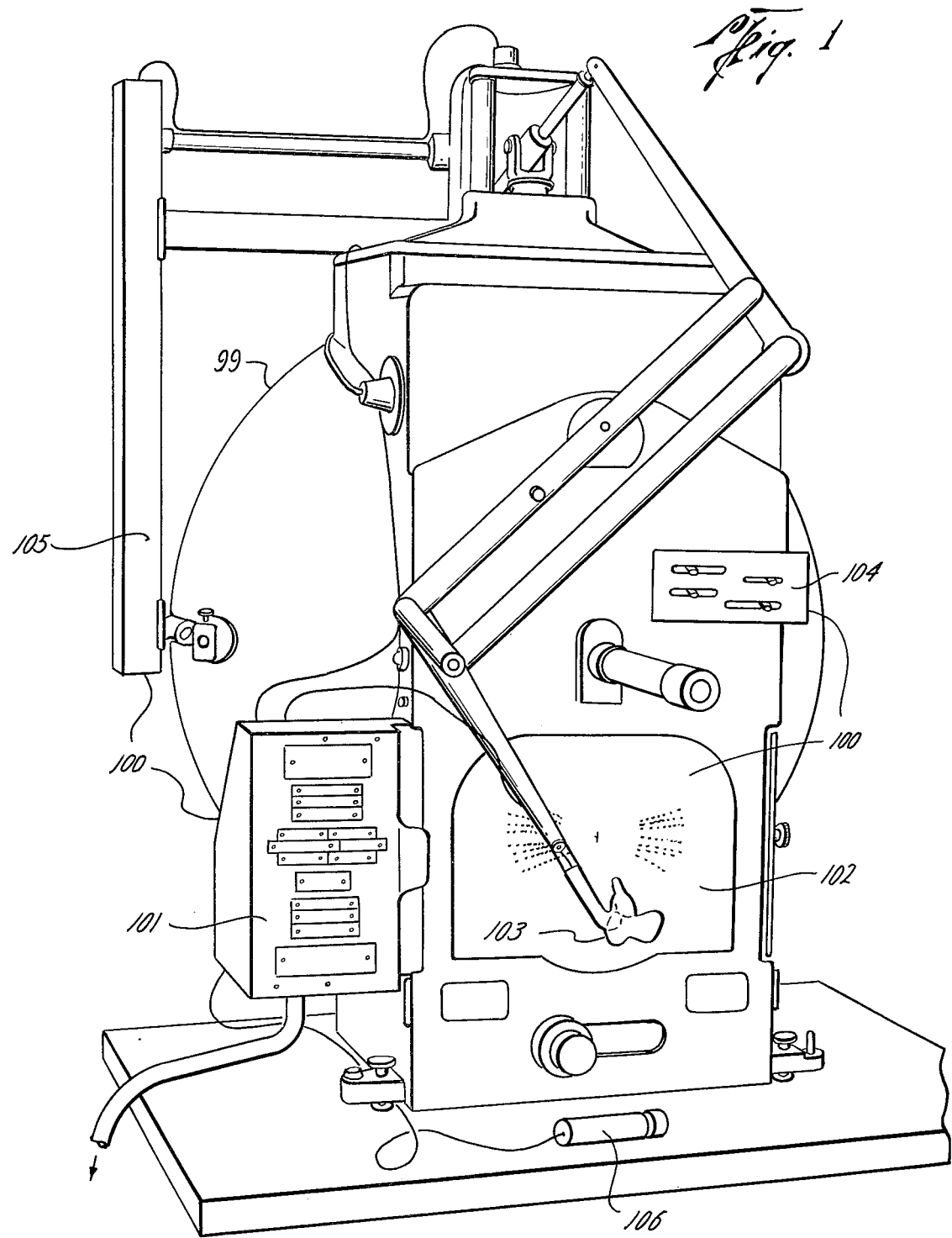
FIG. 1 is an elevational perspective view showing the present invention mounted on a conventional Goldmann-type dome perimeter.

Referring now to the drawings, and particularly to FIG. 1, the apparatus of the present invention is generally indicated by the reference numeral 100, while the Goldmann dome-type perimeter to which it is attached is referenced by 99. FIG. 1 shows the perimeter and the present invention from the operator's side, the patient's head being located near the center of the dome on the opposite side. The invention includes a control panel 101, and an array board 102, said array board attached to control panel 101, and occupying the space in the perimeter 99 typically occupied by a translucent plastic panel against which the typical recording chart paper is held. Further major parts of the apparatus 100 include a cursor mechanism 103 which replaces the original pointer used in the perimeter 99, a stimulus monitore panel 104, a silent shutter mechanism 105 housed within the arm of the projection optics of the perimter, and a patient response button 106.

Figure 2:
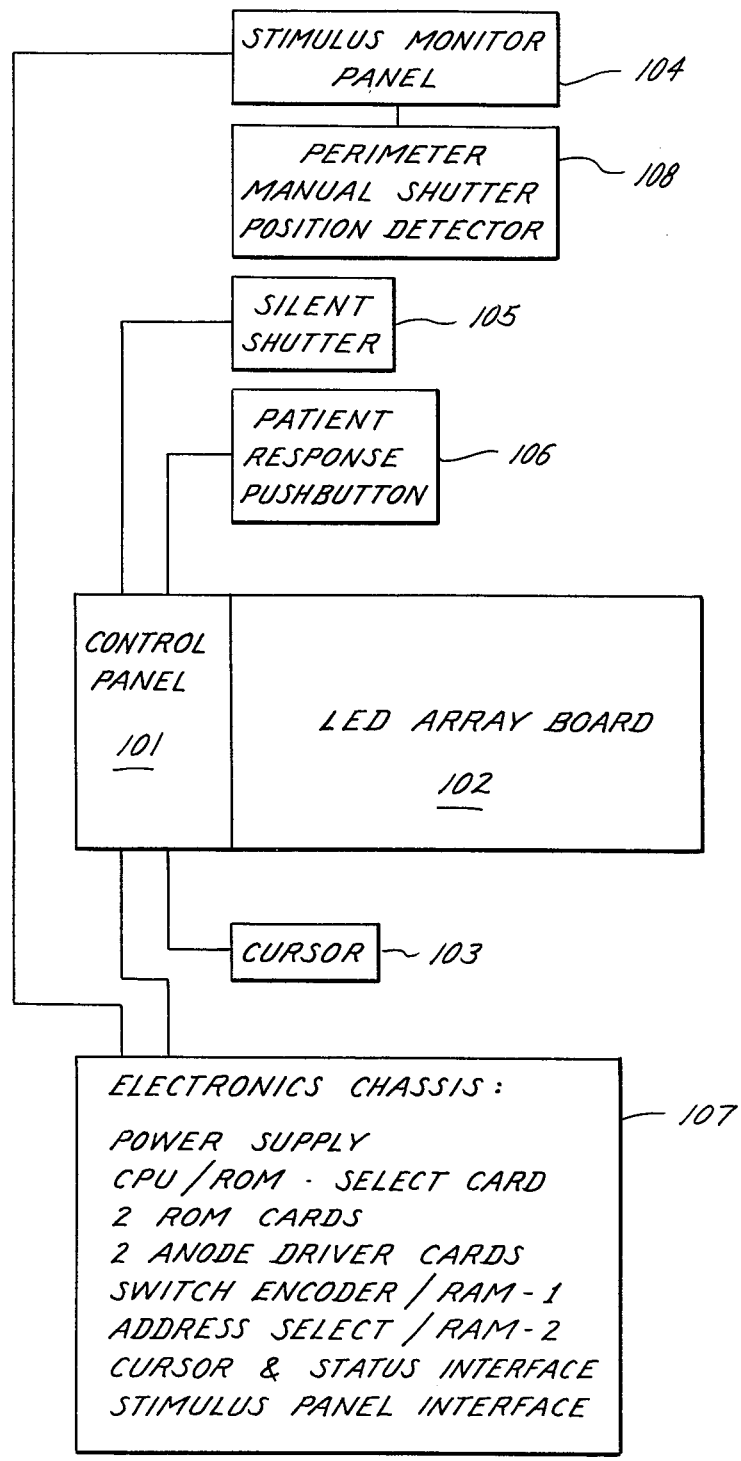
FIG. 2 is a block diagram of the invention showing the physical interconnections of its major parts.

FIG. 2 is a block diagram of the physical interconnections of the invention. Electronics chassis 107 houses major electronics and power supplies for the system. The stimulus monitor panel 104 and sensor 108 detect the position of the perimeter's manual shutter and are connected to an electronics chassis 107. The silent shutter 105, patient response pushbutton 106, and cursory mechanism 103 connect to the control panel 101 and then to the electronics chassis 107. The array board 102 consisting of a plurality, such as over 500, of visual indicators, such as light emitting diodes mounted on a printed circuit board in the exemplary embodiment connects to and is integral with the control panel 101, said control panel 101 also housing switches and indicators to operate the invention, anode drivers to operate the LED's of the array board 102 and an interconnection board to route electronic signals to and from electronics chassis 107.

Figure 3:
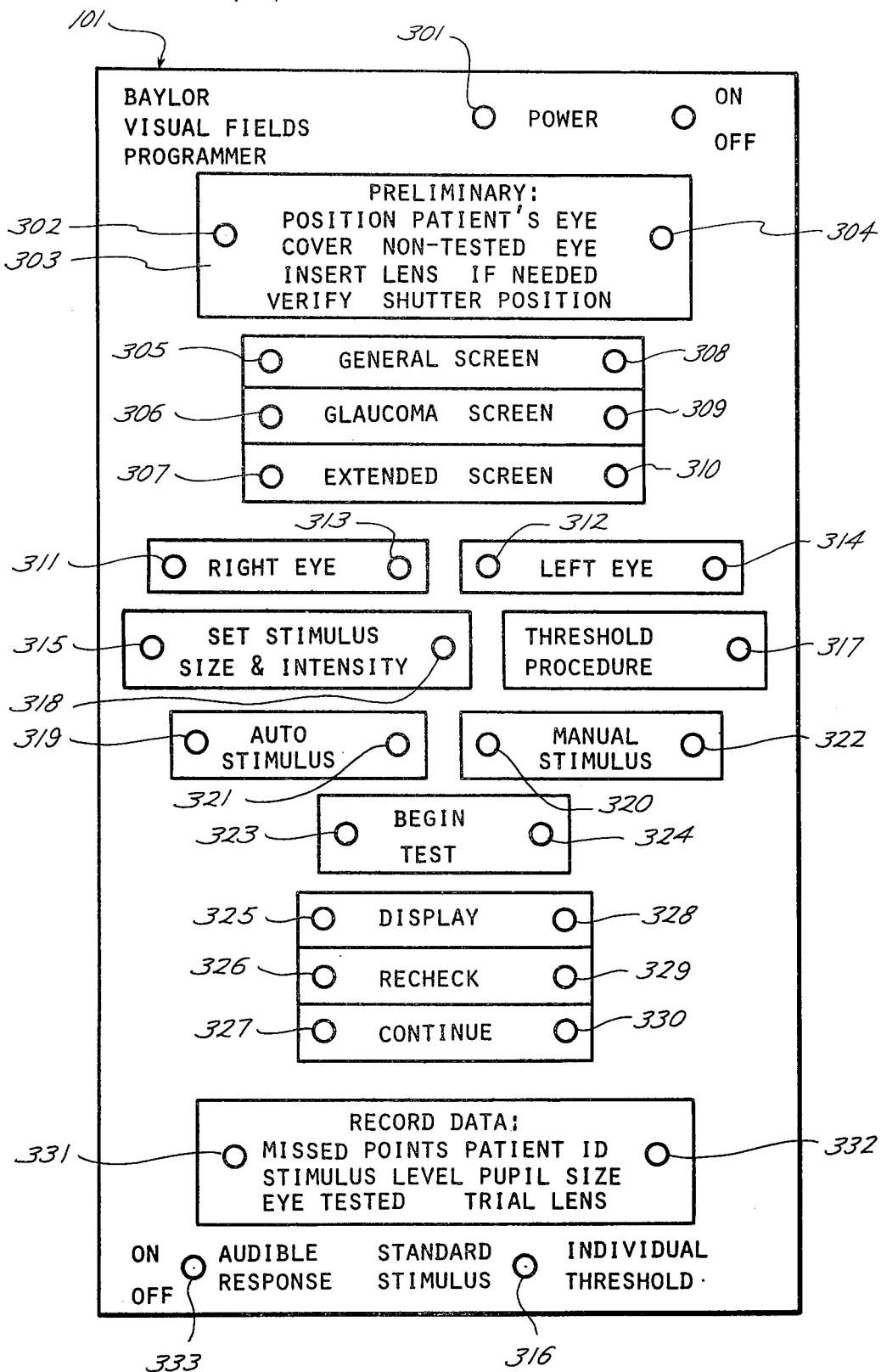
FIG. 3 is an elevational view of the control panel of the present invention.

FIG. 3 shows the layout of the control panel 101 of the invention, the labels, indicators and switches of which are arranged vertically from top to bottom to provide a checklist for the operator. A more detailed description of a typical testing procedure utilizing this control panel is to be described.

Figure 4:
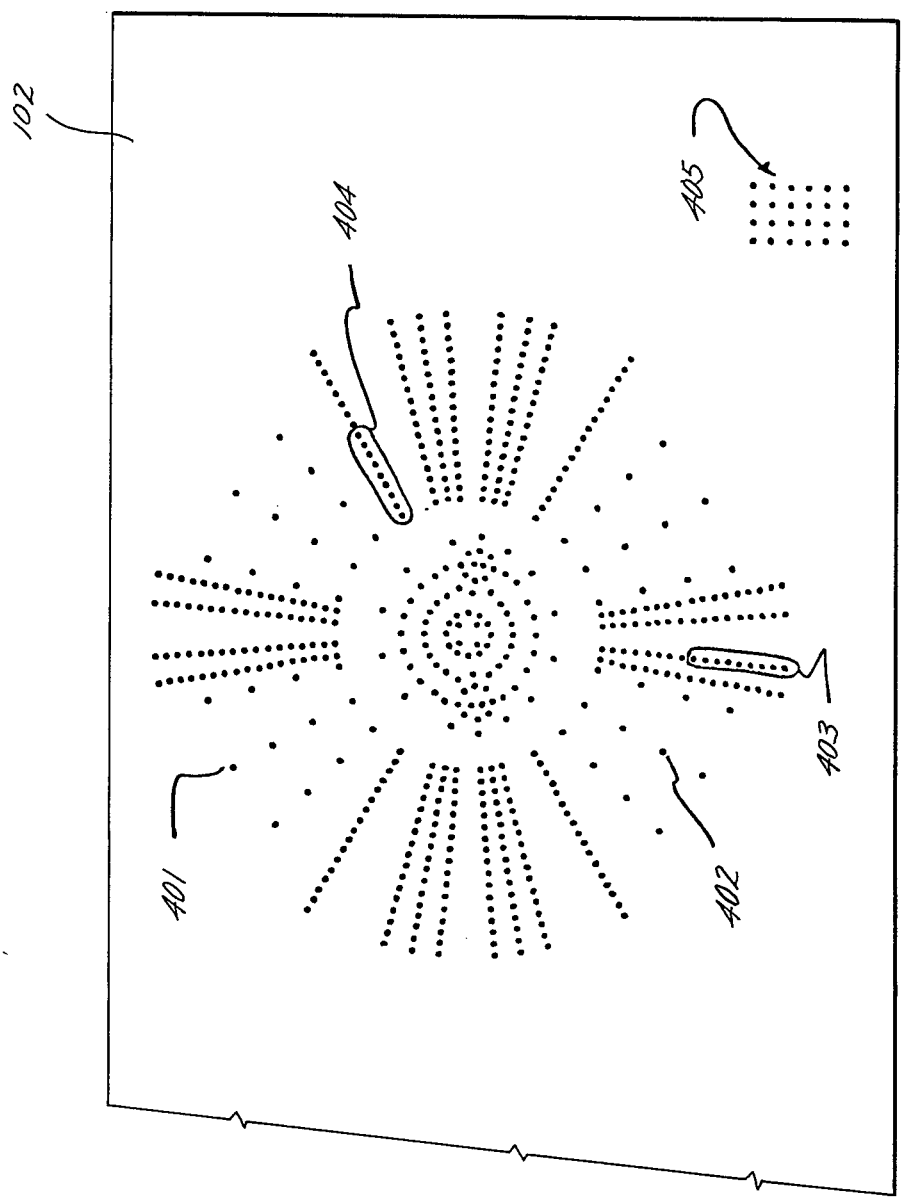
FIG. 4 is an elevational view of the array board showing the location of the indicators.

FIG. 4 shows a layout of the LED indicators on the array board 102 of the present embodiment. The illustrated pattern is a composite of the three visual fields testing programs incorporated into the processor memory of the exemplary embodiment. These three programs, the General Screen, Glaucoma Screen and Extended Screen are intended to reflect different clinical testing needs and differ slightly from right eye to left eye according to the anatomy of the respective retina being tested. The composite pattern is shown for illustrative purposes only. Other possible patterns will be apparent to those skilled in the art and are included within the scope of the claims of this disclosure.

Test locations 401 and 402 are typical individual LEDs used to indicate static testing points. Lines of LED 403 and 404 show typical testing locations used for binetic testing (static and binetic testing procedures are explained below).

FIG. 4 also shows a 4×6 matrix pattern of indicators 405 in the lower right hand corner. These indicators are used to aid the operator to help record the stimulus value used in the data recording portion of the procedure.

Figure 5:
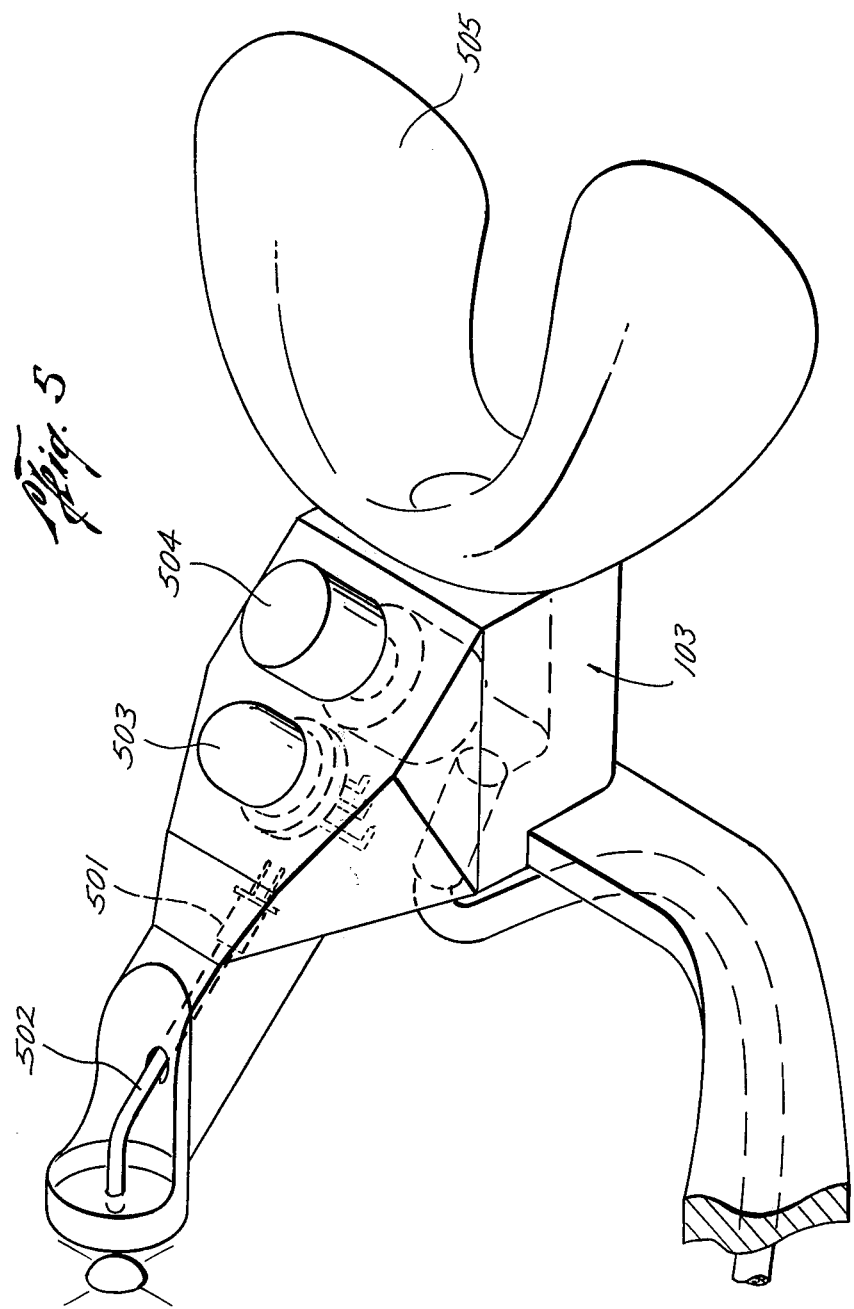
FIG. 5 is an elevational perspective view of the cursor mechanism.

Cursor mechanism 103 is shown in FIG. 5. The cursor is comprised of an alignment sensor 501 to detect alignment of the cursor over one of the illuminated indicators of the array board 102 via fiber optic 502. Indicator 503 is a two color LED used to signal system status conditions such as alignment, shutter open, patient response type and other such conditions. Pushbutton 504 is used by the operator to signal the system electronics to perform such tasks as operate silent shutter 105, change the character of the previous test location. Finger rest 505 is used by the operator to comfortably grasp and operate the cursor mechanism 103. Cursor 103 attaches to the perimeter pantograph arm as shown in FIG. 1.

Figure 6:
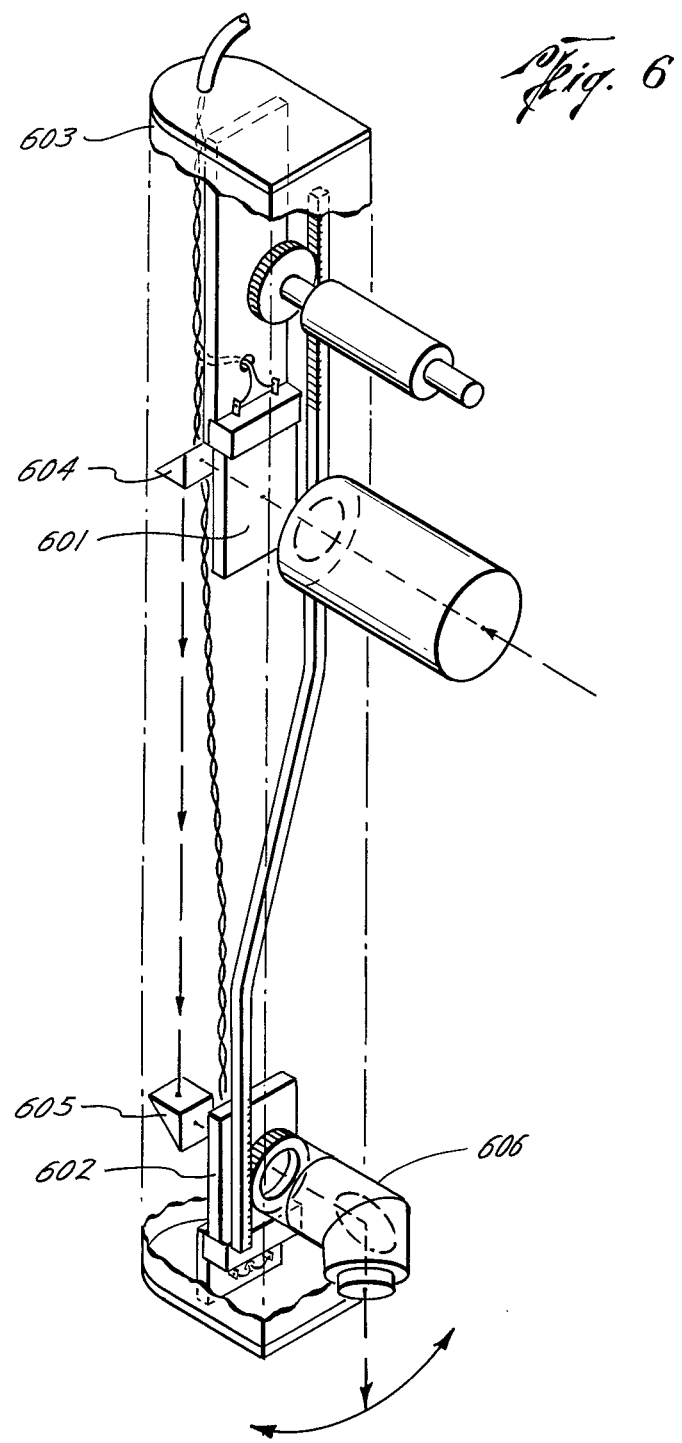
FIG. 6 is an elevational perspective view of the silent shutter mechanism.

FIG. 6 shows the placement of an elctronic shutter such as liquid crystal light valves 601 and 602 within the perimeter projection optics arm 603. This application of the liquid crystal produces a truly silent shutter. Liquid crystals 601 and 602 are used to divert and diffuse the light passing through the projection optics 603, prisms 604 and 605 and final projection optic 606 under control of the system electronics.

Figure 7:
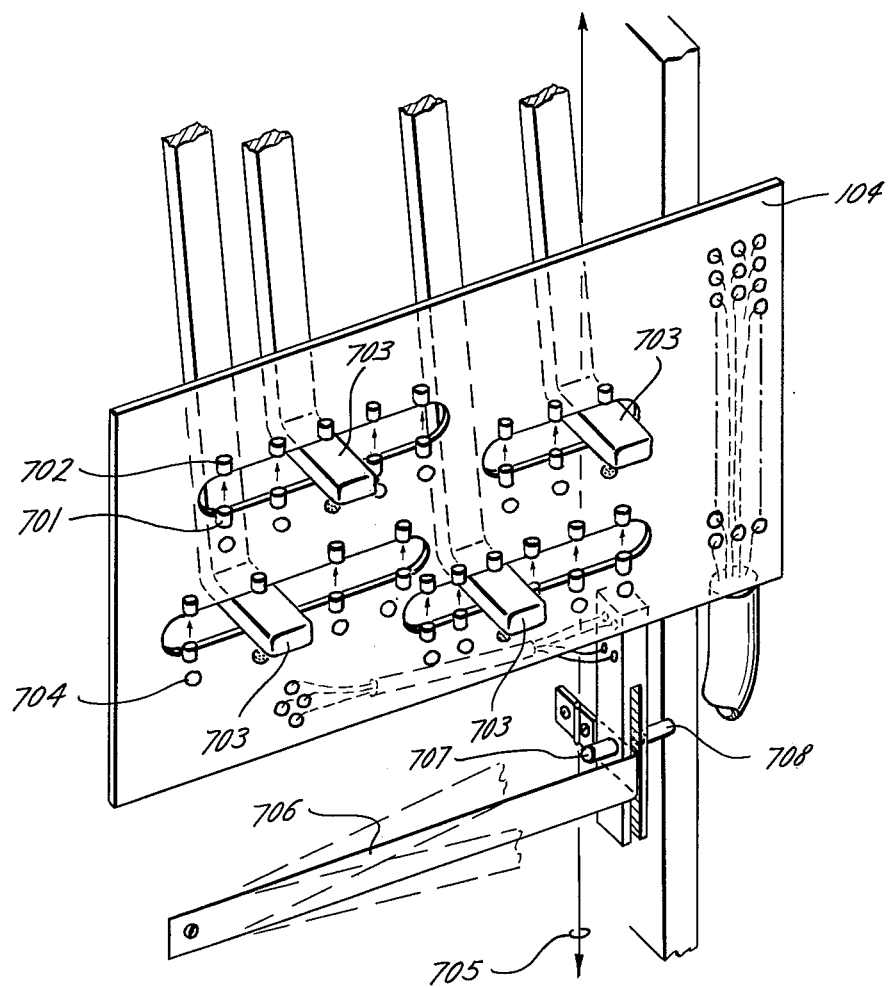
FIG. 7 is an elevational perspective view of the stimulus monitor panel.

Stimulus monitor panel 104 shown in FIG. 7 is mounted in place of the standard stimulus selection panel on the operator's side of the perimeter 99. Panel 104 is comprised of LEDs 701 and sensors 702 to monitor the position of the stimulus control levers 703. Other LEDs such as 704 indicate the proper position of the stimulus control levers to the operator.

Perimeter 99 typically incorporates a manually operated shutter mechanism which, when closed, blocks the stimulus light path negating the function of the silent shutter mechanism 105. Hence the perimeter's manual shutter must be in the open position for the silent shutter to control light presentation. FIG. 7 shows the perimeter manual shutter position detector. Cable 705 connects the perimeter manual shutter to its operating handle. The shutter position detector is comprised of a lever 706 attached to cable 705 which interrupts light passing between LED 707 and sensor 708 when the shutter is in the closed position.

Referring now to FIGS. 1 to 7 and particularly to FIG. 3 which shows the control panel 101 of the invention, the operator performs a visual fields procedure by carrying out the instructions listed on the control panel and operating the switches generally from top to bottom. Illuminated indicators on the panel show which testing conditions have been selected and which are allowed at any point at the procedure.

When power is turned on, indicators 301 and 302 are illuminated. If the perimeter manual shutter 708 is in the closed position indicator 302 does not come on and no further indicators or switches are active until the shutter position is correct. After carrying out preliminary instructions 303, the operator presses PRELIMINARY pushbutton 304. Indicators 305, 306 and 307 are illuminated in response to pressing 304. The operator is thereby prompted to select the program appropriate to the patient being tested. Assume, for example, that the operator has been instructed to use the GENERAL SCREEN test procedure. He then presses 308. The system electronics response by turning off indicators 306 and 307, indicator 305 remaining illuminated. Having selected a test program, the system electronics prompt the operator to select either the RIGHT EYE or LEFT EYE portion of the test program by turning on indicators 311 and 312.

If, for example, operator selects the RIGHT EYE by pressing 313, indicator 312 extinguishes. The system electronics then illuminates indicator 315 prompting the operator to set the STIMULUS SIZE and INTENSITY. At this point the operator has two choices depending on the position of the toggle switch 316 at the bottom of the panel, such choices being determined by the testing policies of the operator's clinic. If the operator selects, or has previously selected the INDIVIDUAL THRESHOLD alternative, indicator 317 illuminates indicating that the operator must carry out a threshold procedure to determine the stimulus levels to be used in the visual fields test. In this procedure the indicator for the smallest and least intense stimulus on the stimulus monitor panel 104 illuminates. After moving the stimulus control levers to the indicated position, a LED on the array board 102 illuminates prompting the operator to move the cursor to this predetermined threshold testing location. At this point a stimulus is presented to the patient. If detected, the size and intensity of this stimulus is stored by the system electronics as a threshold level, and the second of three threshold test locations is illuminated on the array board 102. If the stimulus is not detected, the next larger or more intense stimulus setting on the stimulus monitor panel 104 is indicated. The operator then moves a stimulus control level 703 to the indicated position and another test flash is presented to the patient. The sequence is continued for that test location until a positive response occurs. The sequence is repeated for each of the remaining two predetermined threshold test locations until three threshold levels have been obtained, in each case by increasing size and intensity of test stimuli until detected. The system electronics then discard the lowest (largest and/or most intense) threshold and averages the remaining two levels. This level then becomes the stimulus value used for the central 30° tested in the data collection portion of the procedure which follows.

If the operator selects or has previously selected the STANDARD STIMULUS with toggle switch 316, the operator moves the stimulus control levers 703 on the stimulus monitor panel 104 to the standard positions shown by indicators 704. After completing either the threshold or standard stimulus procedures, the operator presses pushbutton 318, turning out indicator 315.

Subsequently, indicators 319 and 320 light. Assume that the technician requires the MANUAL STIMULUS mode and presses button 322. Indicator 319 turns off and BEGIN TEST indicator 323 comes on. The operator then initiates actual data collection by pressing 324. In the MANUAL STIMULUS mode, the silent shutter 105 opens only after the operator has aligned the cursor 103 with an indicated LED on array board 102, and pressed the cursor pushbutton 504. The MANUAL STIMULUS mode is used with inattentive patients whose fixation must be checked by means of the viewing telescope provided on the perimeter prior to the presentation of each stimulus.

If the technician selects the AUTO STIMULUS mode by pressing button 321, indicator 320 goes out, and the BEGIN TEST indicator 323 comes on. Data collection is initiated as before by pressing BEGIN TEST 324. In the AUTO STIMULUS mode the silent shutter 105 opens automatically when alignment of the cursor 103 with an illuminated LED on the array board 102 occurs.

Turning now to FIG. 4, it is noted that the LEDs of the array board 102 are arranged either as individual points 401, 402 for static testing or as rows of 9 or more points 403, 404 arranged on a radial line from the center of the array board for kinetic testing. In the kinetic testing portions of the procedures a row of 9 LEDs on the array board 102 are illuminated sequentially in the manner similar to that of moving movie marquee light. The operator's task is to position the cursor 103 over the outermost illuminated LED, and move the cursor down the line of the sequentially illuminated points at a rate equal to that of the movement of the light. The system electronics sense alignment of the cursor 103 with the first LED and open the silent shutter 105, allowing the stimulus to project on the inside surface of the dome. When the patient senses the presence of the moving projected stimulus light in the periphery of his vision, he presses the Patient Response Pushbutton 106. The Programmer notes the position of the cursor 103 over the row of sequentially illuminated LEDs at the movement of the response, records this information in its memory as a patient data point and closes the silent shutter 105.

In the static testing portions of the procedures individual LEDs on the array board are illuminated. The operator's task in this instance is to position the cursor 103 over the illuminated point. If the technician had previously selected AUTO STIMULUS 321 on the control panel, a 250-millisecond flash of the test stimulus is automatically presented to the patient when cursor alignment occurs. If MANUAL STIMULUS had previously been selected, the test flash occurs when the operator aligns the cursor over the illuminated LED and pushes the cursor pushbutton 504.

Whether presented manually or automatically, the system electronics "look" for a patient pushbutton 106 response following each stimulus presentation. If a response occurs within a preset time window after the onset of the stimulus, the system electronics score the responses as a "hit" (patient detected a stimulus of the specified size and luminance at that location). If no response occurs within the time window, the system electronics score the point as a "miss." According to the selected testing program, both static and kinetic testing continues until all appropriate testing points have been tested for a specified stimulus size and luminance. The character of each patient response (or lack of response) is signalled to the operator by the illumination of indicator 503 on cursor 103 as green for a "hit" and red for a "miss." The classification can be changed by the operator simply by pressing the pushbutton 504 on the cursor 103 once. Such a change is appropriate when, for example, the operator notes that the patient detected the previous stimulus by looking at it rather than at the fixation light. The operator also has the option of retesting the just previous point by pressing the cursor pushbutton 504 a second time, whereupon the currently illuminated LED on the array board 102 extinguishes and the LED for the preceding point illuminates.

At any time in the test procedure the operator can view those points which have been missed by pressing the DISPLAY pushbutton 328, whose indicator 325 had come on after the first point was tested. After pressing 328, the CONTINUE INDICATOR 327 lights up. To return to the testing program after display, the operator presses the CONTINUE pushbutton 330.

When all of the test points appropriate to the first stimulus level have been tested, the system electronics provide the option of retesting all of the missed static points or going on to the next segment of the procedure. At this point the DISPLAY 325 and RECHECK 326 indicators on the control panel light are illuminated. If the operator wishes to recheck the static missed points, he must press the RECHECK button 329. Subsequently, the missed points are tested in a pseudo-random sequence. If the operator opts for no recheck (eg. with a patient who has missed a great many points, or none at all), he presses the CONTINUE pushbutton 330.

After all of the kinetic and static points for a given stimulus level have been tested and/or retested, the SET STIMULUS SIZE and INTENSITY indicator 315 comes on again, indicating that another series of kinetic and static points are to be tested at a new stimulus level. In this way, various regions of the patient's retina (eg. for periphery, 50° to 70°; near periphery, 30° to 50°; central, 0° to 30°) are tested with stimulus levels ($SL_1$, $SL_2$ and $SL_3$) appropriate for the sensitivity of the region being tested. STIMULUS SIZE and INTENSITY indicator 315, the indicators on the stimulus monitor panel 104 and the LED array 405 in the lower right section of the LED array board 102 are illuminated to guide the operator to set the stimulus control levers to the appropriate setting for that portion of the test. Once the stimulus levers are properly set, the operator presses the pushbutton 319 and 315 goes out. The operator then presses the BEGIN TEST 324 to start the next sequence of kinetic and static tests.

Typically, the sequence is repeated for a maximum of three times, depending on the testing program selected, until all data points have been tested and/or retested. At this point, the RECORD DATA indicator 331 is illuminated along with all of the missed static points and the kinetic data points on the LED array board for the first stimulus level tested. The operator's task is to insert a piece of recording paper into the back of the perimeter over the LED array board 102. The operator then proceeds to mark all of the illuminated points on the recording paper. At this point, the stimulus level at which these data points were obtained is indicated at 405 of the LED array board 102. The instructions printed in the RECORD DATA box of the control panel guide the operator to record the stimulus level used, the patient's missed points, eye tested, pupil size, ID on the recording paper, and the power of any trial lens used, if any.

Once these data have been recorded, the technician then displays and records the data points obtained with the second stimulus level by pressing the RECORD DATA button 332. As before, missed points, threshold points, and stimulus level are recorded, usually with a different colored pen or marker. Data obtained at a third stimulus level is displayed and recorded as before by pressing the RECORD DATA button. Continued pressing of the RECORD DATA button 332 will cycle through the stored data again. Pressing the PRELIMI- NARY button 302 clears the RECORD DATA light 331 and all stored data preparatory to the next test.

Figure 8:
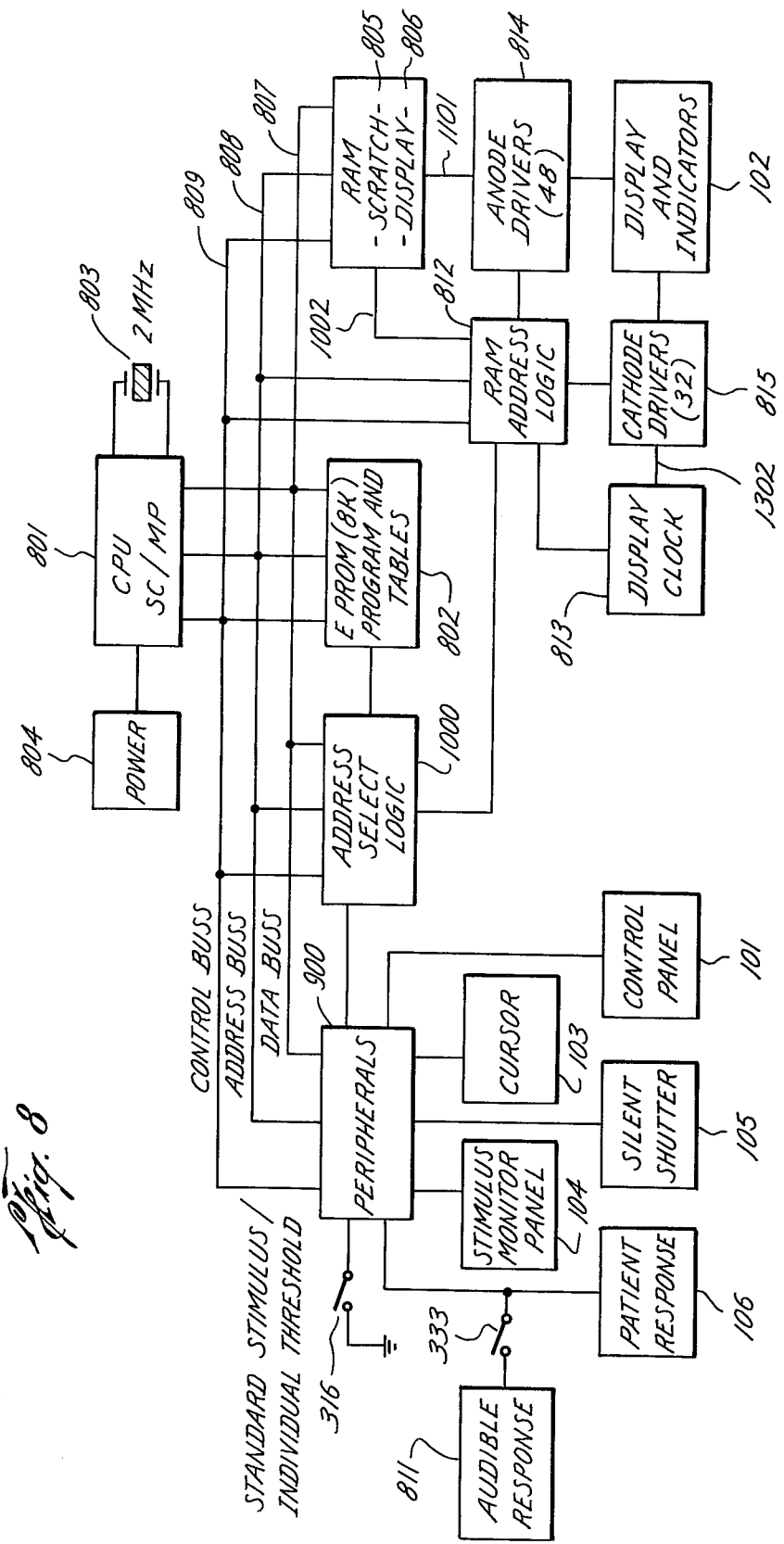
FIG. 8 is a functional block diagram of the invention.

FIG. 8 is a functional block diagram of the system electronics. The device is built around a conventional CPU, 801 (a National Semi-conductor SC/MP in the exemplary embodiment) operating from 2.0 Mhz crystal 803. The system is initialized at power up by circuit 804. The CPU software is contained 8 K of EPROM 802. 256 byte stack memory 805 and temporary memory and display buffer memory 806 combine to form 1.75 K of RAM memory used in the system. Data buss 807, address buss 808 and control buss 809 are utilized in a conventional manner in the system and detailed discussion of their operation is well known to those skilled in the art.

Continuing with reference to FIG. 8, RAM address signal 1002 is generated by address select logic 1000 and RAM address logic circuits 812 and display clock 813. In response to signal 808, RAM 805 addressing is done directly by 808.

The output of RAM 806 is 1101 which selects anode drivers 814. The output of display clock 813, 1302 selects cathode drivers 815 through RAM addressing logic 812.

The anode and cathode drivers 814 and 815 control display matrix circuits which operate the array board 102 testing points, control panel 101 and stimulus monitor panel 104 indicators 704.

Peripheral block 900 in FIG. 8 is shown as a matter of convenience in collecting signals which appear in various parts of the system schematics and are described separately in the individual discussion of each figure below.

Status signals from control panel 101 switches, stimulus monitor panel sensors 702, cursor detector 501, and patient response button 106 are stored in RAM 805 under CPU control via the data buss 807. The status of STANDARD STIMULUS/INDIVIDUAL THRESHOLD switch 333 is monitored similarly. Silent shutter 105 control signal is derived from the control buss 809. Audible response annunciator 811 is controlled by patient response button 106 and control panel switch 317.

Having thus described system characteristics generally, a more detailed treatment of the circuitry will be given.

Schematic details of the conventional CPU applications card are referenced to aid in determining their function with regard to each of the circuit descriptions following. Detailed operation is available in the literature and therefore is not included (National DWG 8704713). Similarly EPROM memory 802 can be comprised of two National 4 K prom cards (National Semiconductor Drawing D8704341).

Figure 9:
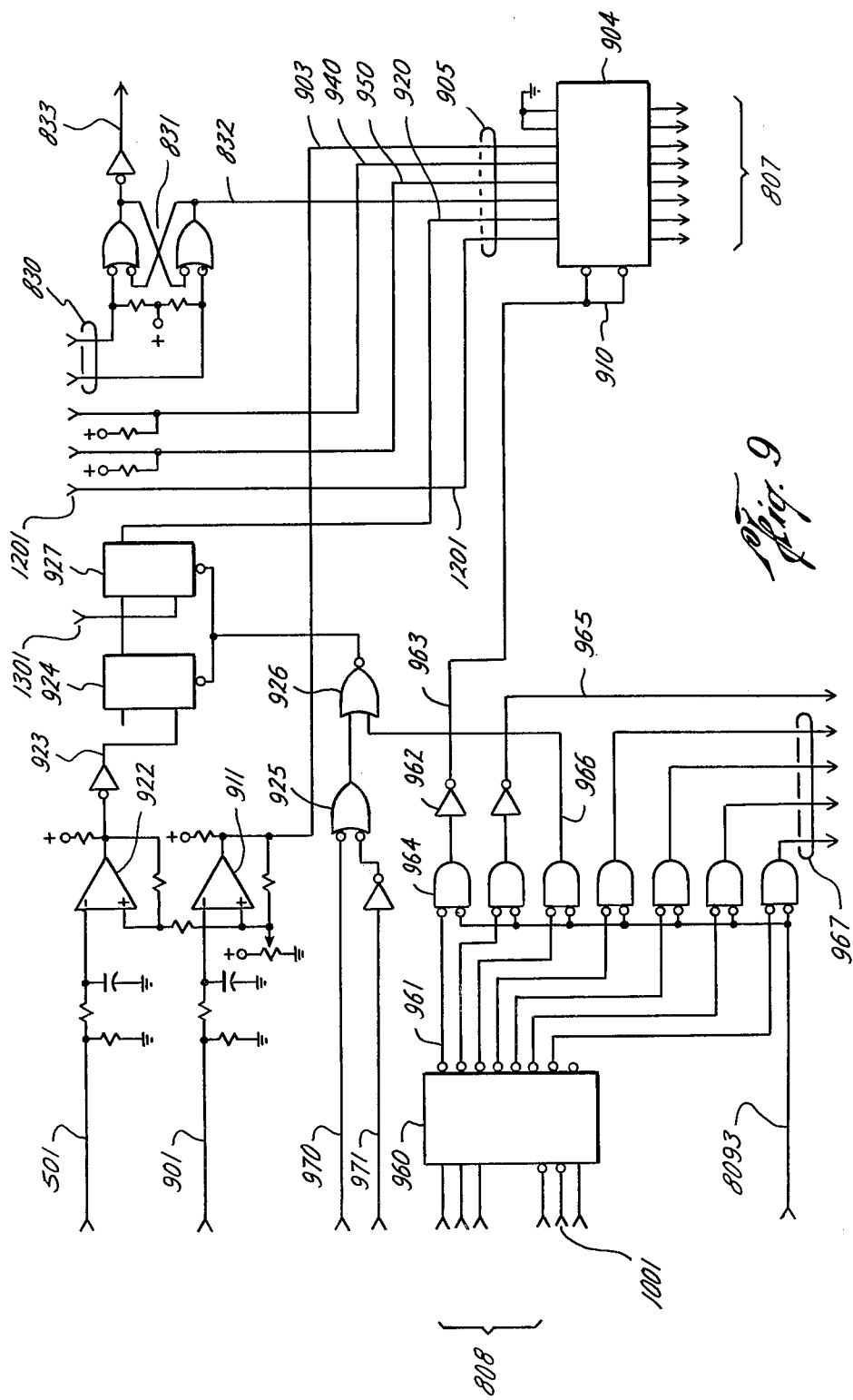
FIG. 9 is a logic diagram of the cursor and status interface.

FIG. 9 illustrates circuitry unique to the application of the conventional CPU to the subject invention. The cursor and status interface circuitry shown produces a substantial portion of the signals represented by functional block 900 in FIG. 8.

Signals appearing at 905 under processor control reflect the status of various peripherals and therefore may be referenced as the status word. For example, signal 903 is a signal indicating that the perimeter manual shutter on the perimeter 99 has been selected to be normally open to allow the silent shutter mechanism 105 to be in control of the stimulus. Signal 903 is produced by 901 through comparator 911. Tri-state buffer 904, when enabled by 910, applies signal 903 to the data bit 5 position on data buss 807 where it may be processed.

Similarly, signal 920 is a signal indicator cursor sensor 501 detector is in alignment when an illuminated test point on the array board 102. In response to this signal, comparator 922 produces signal 923 which sets D flip-flop 924. The output of 924 enables 927. Mux clock signal 1301 sets flip-flop 927 producing signal 920 which after buffering by 904 appears in data bit position on data buss 807.

Signal 830 from subject response pushbutton 106 is debounced by gates 931 producing 832 which produces a signal in bit position 2 on buss 807.

Signal 833 is produced by debounce gates 831. Signal 833 is used to operate a control relay (not shown) which cause audible response annunciator 811 to sound.

Signal 940 is a signal which is hardwired when stimulus monitor panel 104 is installed to indicate that the panel is part of the equipment added to the perimeter. Signal 940 produces a signal in data bit position 4 on data buss 807.

Signal 950 is a binary signal produced by toggle switch 316 on control panel 101. Both states of the signal are used, one to indicate that STANDARD STIMULUS has been selected and the other to indicate that INDIVIDUAL THRESHOLD has been selected. Signal 950 produces a signal in data bit position 3 on data buss 807.

Figure 12:
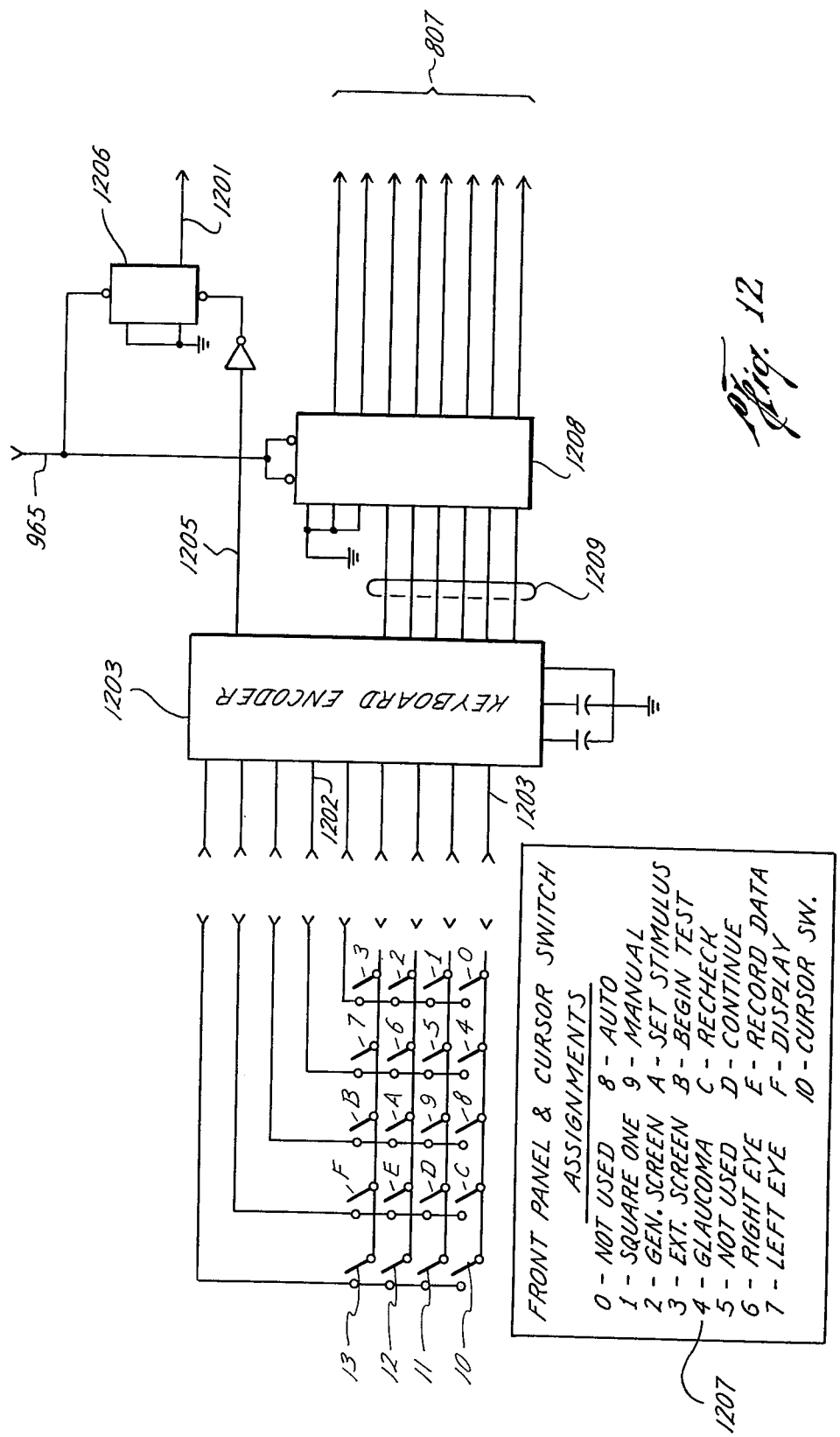
FIG. 12 is a logic diagram of the control switches and swich encoder.

Signal 1201 is produced by the keyboard encoder circuitry shown in FIG. 12. The signal indicates to the CPU that one or more control panel switches such as 304, FIG. 3, has been pressed and status data is available. 1201 produces a signal in data bit position $\phi$ on data buss 807.

960 is a decoder which routes certain addresses from address buss 808 to gates such as 964. In the exemplary embodiment signal 1001 enables decoder 960. Signal 1001 occurs at address 3700 (16). Address notations are shown to the base 16. The composite signal, that is 1001 and 808 together, cause 960 to decode addresses between 3700 (16) and 3706 (16).

At 3700 (16) signal 961 inverted by 962 produces 963 which enables tri-state buffer 904 thereby placing status data on buss 807. Control buss signal 8093 enables gate 964 at the proper time under software control.

At 3701 (16) signal 965 is produced which results in control panel keyboard 101 status signals being placed on the data buss 807 through other circuits to be described.

At 3702 (16) signal 966 occurs to reset cursor detect flip-flops 924 and 927.

At 3703-3706 (16) buss 967 signals are produced which apply stimulus monitor panel 104 status signals to data buss 807 through other circuitry to be described.

970 is a power-up reset signal from the CPU which rests 924 and 927.

971 is a flag signal originated by the CPU to hold 924 and 927 in the reset condition to inhibit their response to cursor detector 501.

Figure 10:
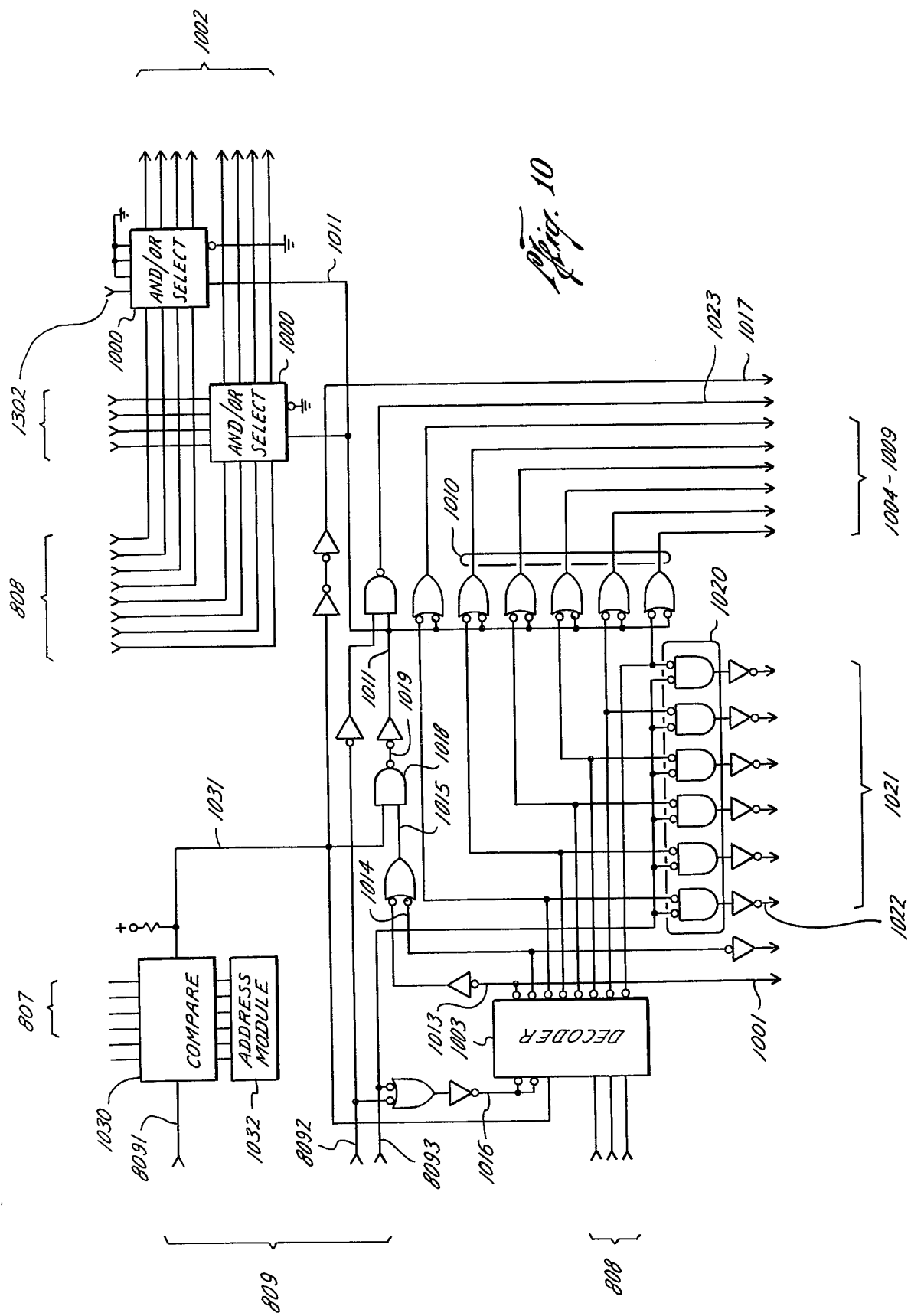
FIG. 10 is a logic diagram of the address select circuits.

FIG. 10 is the address select circuitry and/or select circuits 1000 are used to address RAM memory via buss 1002. Normally it is addressed by display clock buss signals 1302. In this instance signal 1011 is low. When signal 1011 is high the RAM is addressed by the CPU via buss signals 808. When signal 1011 is low, gates 1010 outputs 1004-1009 are all forced high which selects all RAM chips to provide a 48 bit wide output from the RAMs to the array board 102.

Note that the higher order bits from buss 808 are connected as inputs to decoder 1003. During addressing of RAM by the CPU, write signal 8092 or read signal 8093 will be low causing signal 1016 to be high thus partially enabling 1003. The enabling requirements are completed when signal 1031 is high. Signal 1031 also produces signal 1017 which blanks the display during the use of the RAM by the CPU.

Address comparator 1030 generates a select signal when RAM or peripherals are selected by the CPU. In our exemplary system RAM is assigned address locations 3000-37FF (16) by address module 1032. Signal 1031 high enables gate 1012. If the address on the buss 807 is neither 3600 (16) nor 3700 (16) both signals 1013 and 1014 are high. Signal 1011 high enables gates 1010 so that addresses between 3000 (16) and 35FF (16) produce an output from 1003 which results in a chip select signal such as 1004. For example, if the signal on 808 is 3000 (16), signal 1004 is produced, 3100 (16) produces 1005 and so on. The signals select RAM chips to produce an 8 bit wide word required by the CPU.

RAM locations 3600 (16) and 3700 (16) are not part of the display RAM. If buss 808 signals contain a 3600 (16) address, 1003 produces signal 1014. Signal 1014 low produces signal 1015 high causing signal 1011 to go low allowing RAM addressing from buss 1002. Address 3700 (16) also switches 1011 low.

Signal 8093 goes low in the RAM read mode and enables gates 1020 signals from the output of decoder 1003 such as 1021 to select RAM output sequentially through gates 1020 and select buss 1021.

Signal 1023 is in the memory write pulse to the RAM memory.

Figure 11:
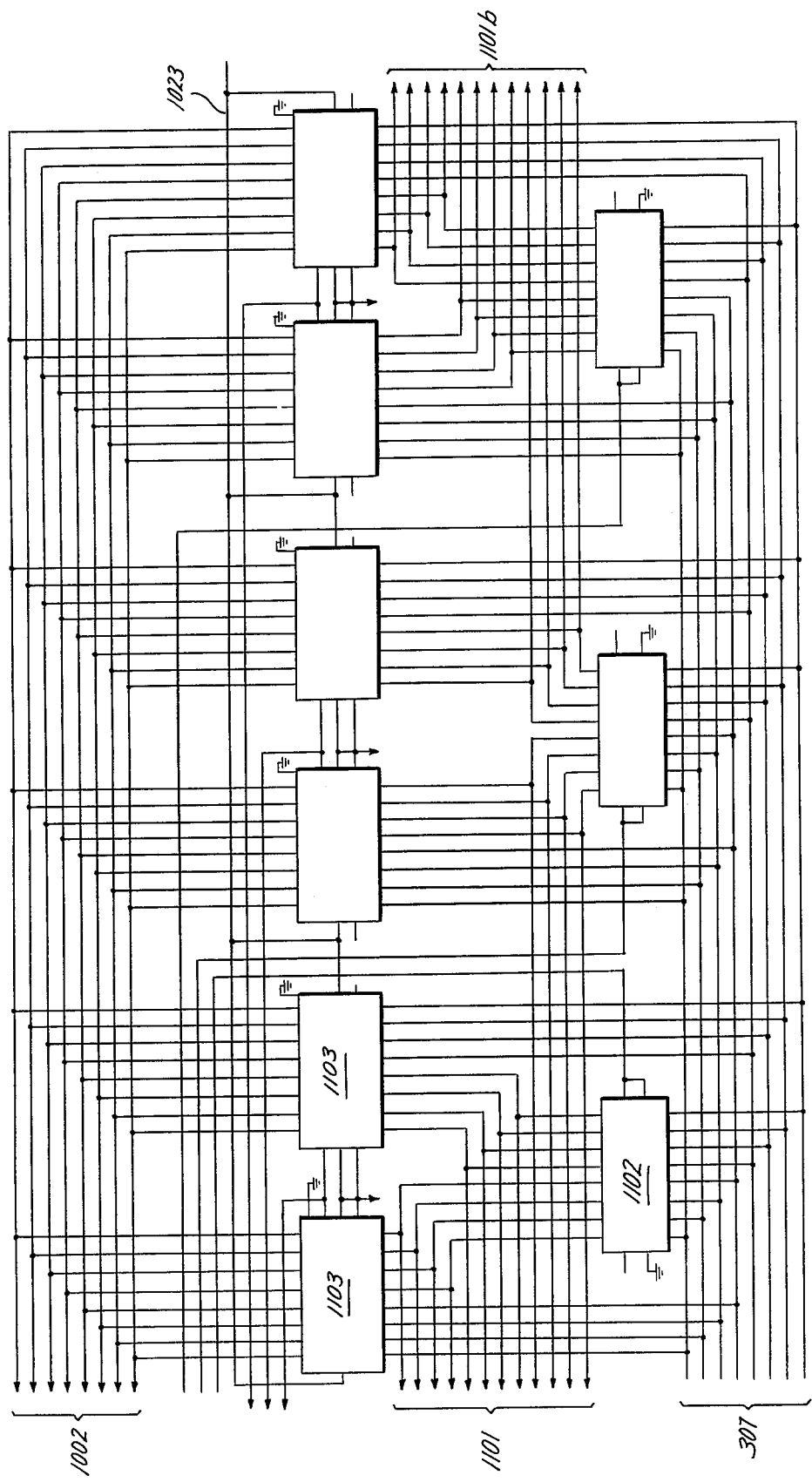
FIG. 11 is a logic diagram of a portion of the display memory.

Refer now to FIG. 11. This figure illustrates the system RAM circuits which are organized as six 8 bit bytes 256 words when being used by the CPU in program execution.

The circuits are addressed conventionally by signals from buss 1001 and chip signals 1004 through 1009 as previously described. Signal 1023 enables the write mode. Signals 1021 select the appropriate memory location in the read mode by enabling circuits such as 1102 to place data from the RAM such as 1103 on data bus 807.

A novel use of the 8 bit wide RAM is its use in the present invention to furnish data to the display matrix in a format 48 bits wide. This is achieved by circuitry in FIG. 10 which forces all chip select signal 1004-1009 high thereby placing data from all the RAMs on buss 1101. Since these data are always present on buss 1101, the display is blanked as previously described when the RAM is in use by the CPU in program execution.

Display data is stored in the first 32 bytes of the RAM. The remainder of the RAM is available to the CPU for use in the operating program and for temporary storage. FIG. 15 shows how the data in RAM and all of the system LEDs correlate.

In FIG. 12, a keyboard encoder 1203 responds to signals such as 1202 and 1203 produced by switches located on the control panel 101 and the cursor switch 504, by generating signal 1205 which rests flip-flop 1206 and produces 1201. Signal 1201 advises the CPU that switch data is available through circuitry already described in FIG. 9. When the data is read by the CPU, signal 965 sets 1206. The data is read by the CPU from data buss 807.

Encoder 1203 generates a code such as 1207 in response to control panel switches bussed to the input of 1208 via buss 1209. Signal 965 enables 1208 to place switch status data on buss 807.

Figure 13:
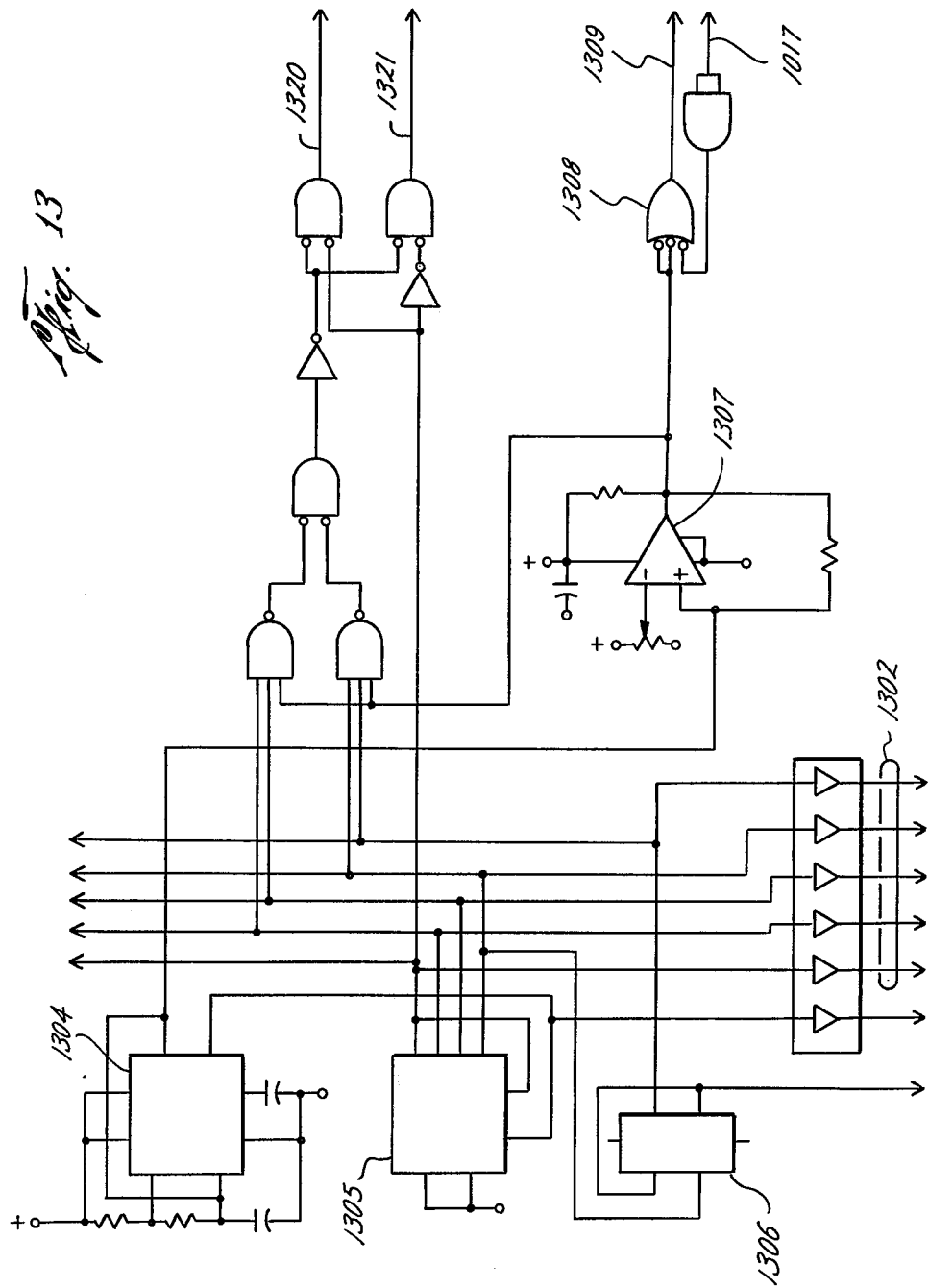
FIG. 13 is a display clock generator circuit.

FIG. 13 illustrates a conventional clock circuit. Circuit 1304 is the clock oscillator which operates at approximately 100 Hz, to drive clock counter circuit 1305. Counter 1306 is driven by counter 1305. The output signal of the two counters 1302 is a 5 bit code which drives the cathode drivers shown in FIG. 14.

Circuit 1307 blanks the display via gate 1308 during counting transitions in counters 1305 and 1306 to prevent flickering. Signal 1017 also produces signal 1309 to blank the display during use of the RAM by the CPU as explained in the discussion under FIG. 10. Signals 1320 and 1321 drive cathode drivers controlling the control panel 10 indicators and stimulus monitor panel 104 indicators so that they are not blanked by signal 1017.

A major consideration in the design of the invention was the problem of controlling more than 500 LEDs in the system under program control without flicker and with minimum power expended. This was solved by arranging LED driving circuitry in a 32×48 matrix. In this manner, up to 1536 points including LED indicators on array board 102, stimulus monitor panel 104 and control panel 101 could be accommodated.

The matrix organization provides 32 cathode drivers 1401 as shown in FIG. 14 for 32 circular rings, and 48 meridian anode drivers 1402 such as shown in FIG. 14, each supplying approximately 80 Ma peak to each LED.

The display data is contained described in FIG. 11. As shown in FIG. 11, the anode drivers are addressed directly by the RAM matrix output, buss 1101a and 1101b, which is 48 bits wide.

FIG. 15 shows the contents of the display RAM in table form. By way of illustration, if the operating program is required to illuminate a test point on array board 102 at the 90° meridian 1501, and 40° radially 1502, the address in memory for this LED 1503 is 310B as tabulated at 1504 and 1505. Data bit 3, 1106, must be placed on data buss 807 to illuminate the indicator.

Referring now to FIGS. 16 and 17 jointly, signals from buss 967 are used to sequentially enable buss buffer circuits such as 1701. Referring now to FIG. 16, signals from detectors 702 on the stimulus monitor panel 104 produce signals such as 1602 indicating the position of the various selecting levers. Outputs of the comparators 1603 such as 1604 are connected to the inputs of buss buffer circuits such as 1701. When such circuits as 1701 are sequentially enabled by signals from buss 967, status signals from stimulus monitor panel 104 are placed on data buss 807. As previously stated this occurs at addresses 3703-3706 (16) in the exemplary embodiment. FIG. 16 shows a typical emitter 701 detector 702 and level converter circuit used to detect the position of the stimulus control levers 703 on the stimulus monitor panel 104.

Figure 18:
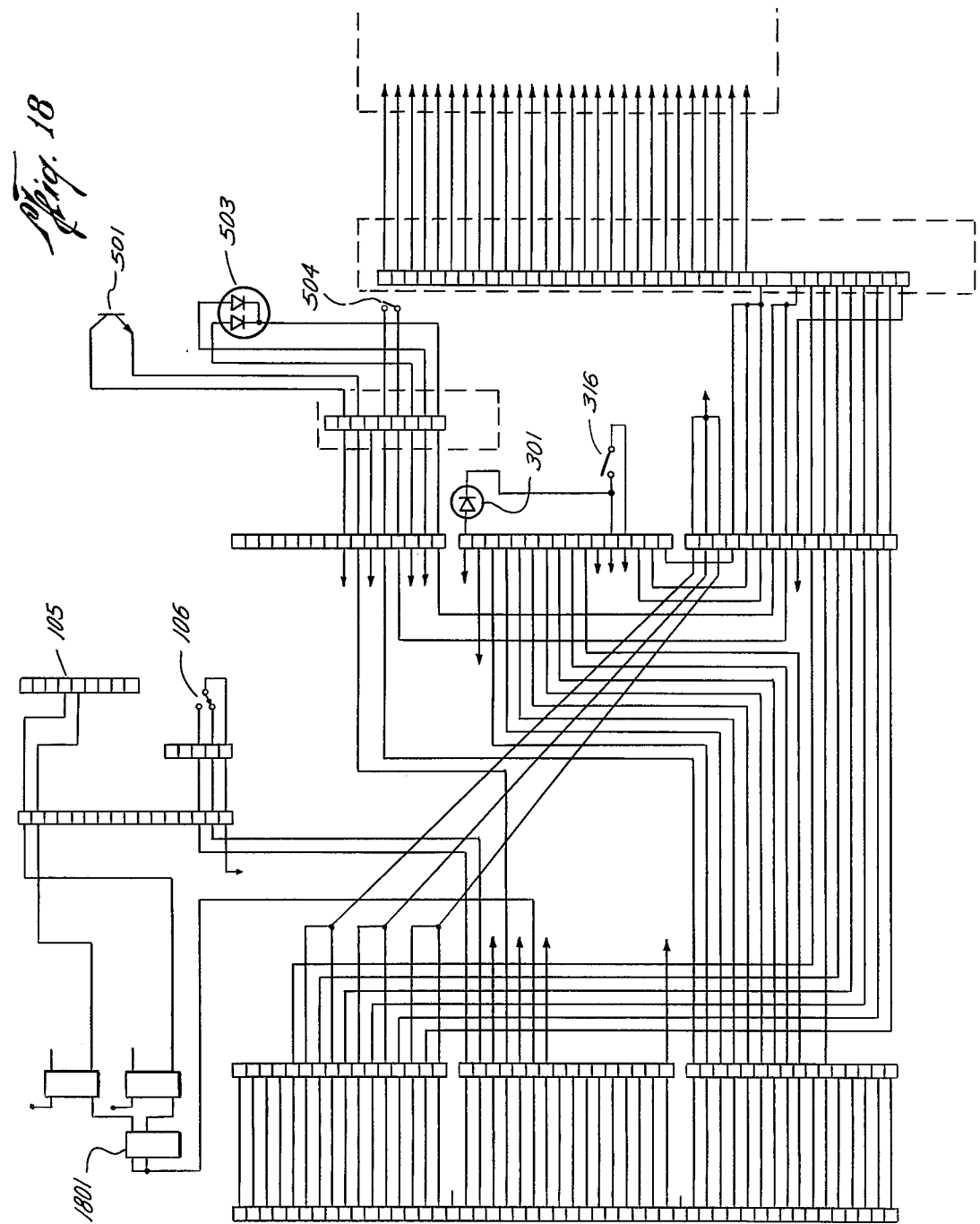
FIG. 18 is an electrical diagram of a portion of the distribution board.

FIG. 18 shows various interconnects of the system circuitry. Also shown in the relay circuitry 1801 which drives the silent shutter 105, the subject response pushbutton circuitry 106, the power-on indicator 301, the STANDARD STIMULUS INDIVIDUAL THRESHOLD switch 316, the cursor detector 401, the cursor indicator 503, and the cursor pushbutton switch 504.

The present invention, therefore, is well adapted to carry out the objects and attain the ends and advantages mentioned as well as others inherent therein. While the exemplary embodiments of the invention are given for the purpose of disclosure, numerous changes in the details of construction and arrangement of parts may be made which will readily suggest themselves to those skilled in the art and which are encompassed within the spirit of the invention and the scope of the appended claims.

What is claimed is:

1. An apparatus for retrofitting a projection type ophthalmic visual fields testing instrument having a movable test light controlled by a movable mechanical arm for projecting a test stimulus comprising, an array board positioned adjacent the mechanical arm having a multiplicity of visual indicators spatially arranged in a composite pattern of testing points required for at least one ophthalmic testing procedure including kinetic visual fields testing for a visual fields instrument, a processor connected to the array board for sequentially actuating said indicators in accordance with said testing procedure, said processor having a memory, a manually actuated cursor mounted on the mechanical arm including a sensor indicating when the cursor is aligned with an actuated visual indicator, means connected to said test light for actuating said light when the sensor on the cursor is aligned with an actuated indicator, and a patient's response switch connected to the memory for recording the patient's response to the light stimulus.

2. The apparatus of claim 1 wherein the cursor includes a manually actuated switch connected to the processor for overriding the patient's response.

3. The apparatus of claim 1 wherein the test light includes a solid state electronic shutter whereby the actuation of the light stimulus is silent.

4. The apparatus of claim 1 wherein the electronic shutter includes liquid crystal light valves controlling the passage of light.

5. The apparatus of claim 1 including visual indicator means on the cursor indicating the patient's response.

6. The apparatus of claim 1 including switching means connected to the processor for illuminating the test points on the array missed by the patient.

7. A method of testing the visual field of a patient using a projection type ophthalmic visual fields testing instrument having a movable light test stimulus controlled by a manually movable mechanical arm comprising, placing an array board adjacent the mechanical arm, said board having a multiplicity of visual indicators spatially arranged in a composite pattern of testing points required for at least one ophahalmic testing procedure for a visual fields instrument, sequentially actuating said visual indicators in accordance with said one testing procedure, manually moving the arm into alignment with each of the actuated visual indicators thereby moving the test stimulus viewed by the patient, when the arm is moved into alignment with an actuated indicator siliently actuating the test stimulus by a solid state electronic shutter, recording the patient's response to the test stimulus in a memory, after the testing is completed, actuating the visual indicators which the patient missed, and placing recording paper over the array board and marking the position of the actuated visual indicators on the recording paper.

8. In the art of processor controlled visual field measurement of the type having a substantially hemispherical perimeter with a diffusely reflecting interior surface and a pantograph for projecting a spot of light at a known locus within the said interior surface and means for determination and recordation of the response, if any, of the subject being tested for visual field by means of a planned sequence of such visual stimuli, the improvement comprising, a sequentially actuated array of visible indicia disposed upon the surface of a retrofitable attachment to the said perimeter in the form of a multiplicity of visual indicators spatially arranged in a composite pattern of testing points required for at least one ophthalmic test, said array board mounted adjacent the pantograph arm of the perimeter, a manually movable cursor means disposed upon said pantograph arm, said cursor means including visual indicating means and sensor means whereby the alignment of the said cursor means with an active visible indicia is signified by illumination of the said indicator means operatively associated with said sensor means to provide visual verification to the operator of the system of proper alignment of the cursor, a processor having a memory connected to the array board for sequentially actuating the indicators for providing a light stimulus of either a series of discrete static stimuli or kinetic stimuli at a rate established by the processor, said processor including means for eliminating the reaction time lag of the subject, an electronic silent shutter mechanism integral to the optical projection light path to provide control by the processor means and the said cursor-indicator relationship to occlude or open the optical path whereby the stimulus light may be projected as required by the ophthalmic test without providing any audible clue to the subject being tested so that the test result will not be biased by the said audible clue.

* * * * *